US006632603B1

(12) United States Patent
Hubscher et al.

(10) Patent No.: US 6,632,603 B1
(45) Date of Patent: *Oct. 14, 2003

(54) NON-CAPTIVE SUBSTRATE LIQUID PHASE IMMUNOASSAY

(76) Inventors: Thomas T. Hubscher, 107 Argosy Dr., Gaithersburg, MD (US) 20878; Erik P. Lillehoj, 3126 Rte. 32, West Friendship, MD (US) 21794

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 852 days.

(21) Appl. No.: 08/914,700

(22) Filed: Aug. 19, 1997

Related U.S. Application Data

(63) Continuation of application No. 08/605,595, filed on Feb. 29, 1996, now abandoned.

(51) Int. Cl.[7] .............................................. G01N 33/533
(52) U.S. Cl. ................. 435/6; 422/58; 422/61; 422/101; 435/7.1; 435/7.92; 435/7.93; 435/7.94; 435/288.6; 435/971; 435/975; 436/518; 436/538; 436/539; 436/824; 436/524; 436/525
(58) Field of Search ............................. 422/58.61, 101; 435/7.1, 6, 7.92, 7.93, 7.94, 288.6, 971, 975; 436/518, 538, 539, 824, 524, 525

(56) References Cited

U.S. PATENT DOCUMENTS 4,313,734 A * 2/1982 Leuvering
4,623,461 A * 11/1986 Hossom et al. ............. 210/445
4,853,335 A    8/1989 Olsen et al.
4,859,612 A *  8/1989 Cole et al. .................. 436/523
5,565,366 A * 10/1996 Akers, Jr. ................... 436/534

FOREIGN PATENT DOCUMENTS

EP        0207152 B    12/1992
WO        WO8603839    7/1986

* cited by examiner

Primary Examiner—Bao-Thuy L. Nguyen
(74) Attorney, Agent, or Firm—Edell, Shapiro & Finnan, LLC

(57) ABSTRACT

An immunoassay of a liquid biological specimen for a specific analyte is conducted by forming a test sample by contacting the specimen with: (1) a binding substance of a ligand, antiligand or receptor capable of binding the analyte and (2) a detector substance of a colloidal gold or silver labeled ligand or antiligand to form a test sample. The test sample is applied by flowing onto a defined zone of an insoluble porous support film having a pore size impassable to a complex formed between the analyte, if present, with the binding substance and the detector substance, but passable to the binding substance and detector substance while remaining uncomplexed in the absence of the desired analyte. If the analyte is present in the test specimen, the detector substance binds with the analyte and the binding substance to form a visually inspectable complex on the surface of the porous support film. After application of the test sample to the porous support, the surface of the porous support is visually inspected for color to determine the presence and quantity or the absence of the analyte being assayed.

21 Claims, 1 Drawing Sheet

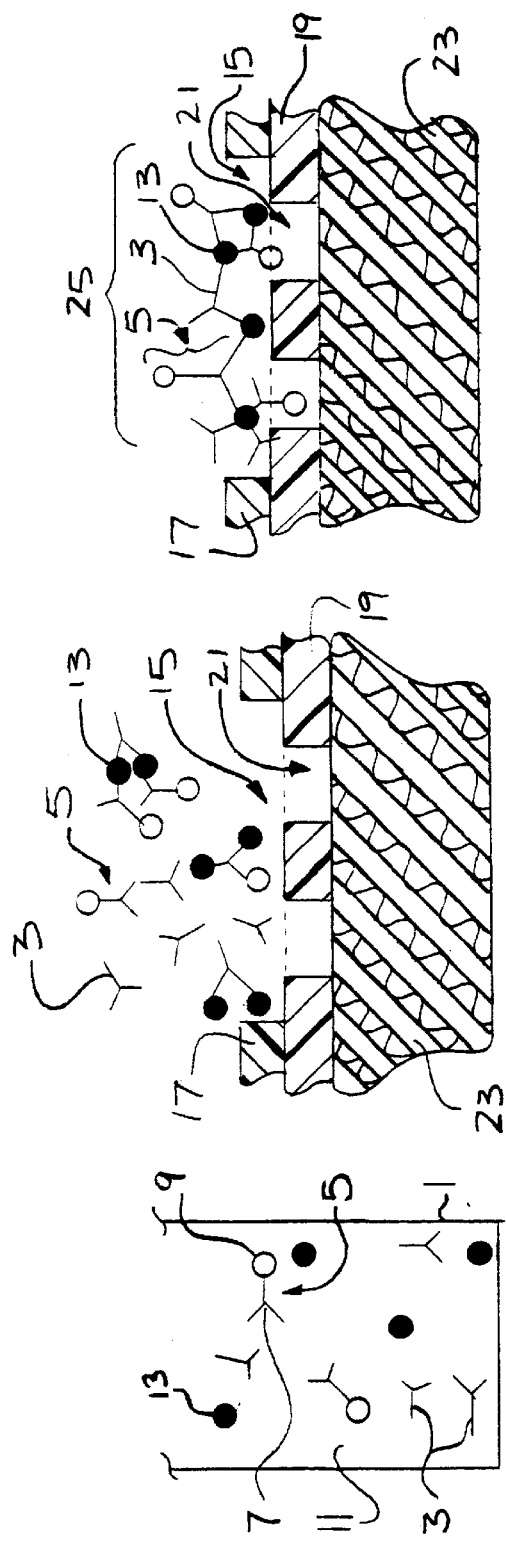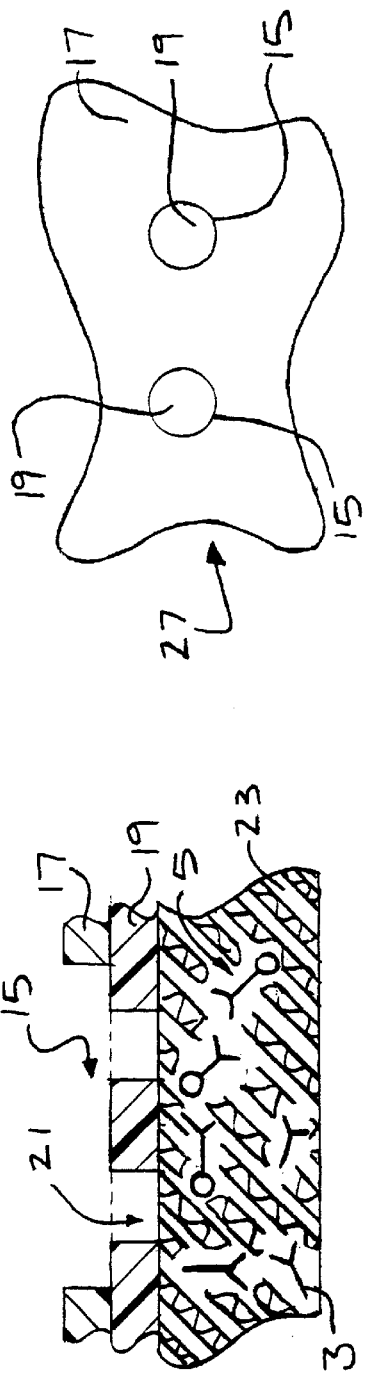

NON-CAPTIVE SUBSTRATE LIQUID PHASE IMMUNOASSAY

This is a continuation, of application Ser. No. 08/605,595 filed Febr. 29, 1996 now abandoned.

FIELD OF THE INVENTION

The invention relates to a detection method and kit for the identification and quantification of analytes in biological specimens by non-captive substrate liquid phase immunoassay techniques.

BACKGROUND OF THE INVENTION

Observations of colloidal gold or silver concentrations have been used in immunoassays in conjunction with solid phase diffusion assays. For example, European Patent No. 207,152 discloses a solid phase diffusion assay utilizing a porous sheet having ligands or receptors prebound to the sheet prior to the application of an analyte and a colloidal gold or silver labeled ligand or receptor. However, assays performed on ligand or antiligand coated porous films must be specifically tailored for a particular analyte and, in view of the limited surface area and reaction time with antigens, this process may be ineffective if the affinity of the substrate bound antiligand for the labeled analyte is low. Furthermore, specific areas of the porous sheet substrate may become overloaded with analyte due to restricted radial diffusion, thereby allowing colloidal metals already bound to analytes to pass through the porous substrate without binding to the surface of the porous substrate for subsequent visual detection.

U.S. Pat. No. 4,853,335 to Olsen et al., discloses a sandwich immunoassay method by premixing a biological specimen with: (1) a colloidal gold labeled ligand or antiligand and (2) solid phase captive particles coated with a ligand or antiligand and applying the subsequent mixture onto the surface of a porous film. By requiring solid phase captive particles this process may distort the visual detection measurements because uncoupled captive particles may block the pores of the substrate and prevent rapid passage of uncoupled colloidal gold.

In both of the foregoing patents a ligand, antiligand or receptor is necessarily prebound to a captive substrate in the form of an insoluble porous sheet or a solid captive particle such as a latex particle. It is desirable to develop a method for quantitative and qualitative detection of an analyte, such as C-reactive protein, using a non-captive substrate in order to accelerate passage of non-complexed immunoassay constituents through the pores of the test support. The use of a non-captive substrate technique presents the most simplistic and flexible approach to the rapid and efficient identification and quantification of ligands and analytes and diagnosis of a disease.

By eliminating the need for prebinding ligands to solid supports or substrates as a part of the assay system, non-captive substrate techniques promote accurate detection of analytes and cost savings in the production and subsequent use of diagnostic test kits.

SUMMARY OF INVENTION

The object of the present invention is to overcome the deficiencies of prior art solid phase captive immunoassay techniques through the development of a non-captive substrate immunoassay that is easily conducted and accurate in detection and measurement.

The present invention is an immunoassay performed on a liquid biological specimen, e.g. serum, plasma, whole blood, etc., for a specific analyte by forming a test sample by contacting the liquid biological specimen with: (a) a binding substance of a ligand, antiligand or receptor capable of binding the analyte and (b) a detector substance of a colloidal metal labeled ligand or antiligand to form a test sample. Both the binding substance and the detector substance are in liquid phases. The test sample is then applied onto a defined zone of an insoluble porous support film having a pore size impassable to a complex formed between the analyte, if present, with the binding substance and the detector substance, but passable to the binding substance and detector substance while remaining uncomplexed in the absence of the desired analyte.

If the analyte is present in the test specimen, the analyte binds with both the detector substance and the binding substance to form a visually discernable precipitable complex on the surface of the porous support film. After application of the test sample to the porous support, the surface of the porous support is visually inspected for color to determine the presence and approximate quantity or the absence of the analyte being assayed.

BRIEF DESCRIPTION OF THE DRAWING

FIGS. 1–4 diagrammatically illustrate sequential steps in a procedure used in the present invention to make the qualitative and quantitative determination for a specific analyte.

FIG. 5 is a top view of an immunoassay kit used in the present invention.

DETAILED DESCRIPTION OF THE INVENTION

The present invention relates to a qualitative and quantitative immunoassay of liquid biological specimens to determine the presence and the approximate concentration of a specific analyte that can be present in each of the biological specimens. The assay may be used to quickly determine the presence of analytes such as proteins, drugs, hormones, vitamins, multivalent antigens and the like. The present assay is used as a method of the qualitative or quantitative detection of an analyte in a liquid biological specimen by adding to the biological specimen: (a) a binding substance in liquid phase selected from the group consisting of a ligand, an antiligand and a receptor capable of binding the analyte, and (b) a detector substance in liquid phase selected from the group consisting of a colloidal metal labeled ligand and a colloidal metal labeled antiligand, to form a test sample containing a precipitable complex if the analyte is present, and forming no such complex in the absence of the analyte in the biological specimen. The test sample is preferably formed by incubating the detector substance, the binding substance, and the liquid biological specimen all in liquid phase together for an appropriate time period, such as one second to one hour.

The test sample is applied by flowing onto a defined zone of an insoluble porous support. The support has a maximum effective pore size smaller than any complex formed between the analyte, the binding substance and the detector substance and having a minimal effective pore size larger than each of the analyte, the binding substance and the detector substance. Once the test sample contacts the insoluble porous support, any complexed analyte is unable to pass through the pores in the porous substrate, and the complex, including the detector substance, remains on the surface of the porous substrate for visual inspection. Thus, by assessing the defined zone of the porous substrate for color development caused by the formation of the complex between the analyte, the binding substance and the detector substance, one may perform a qualitative and quantitative determination of the presence of the analyte.

The immunoassay of the present invention is a non-captive substrate immunoassay. A non-captive substrate immunoassay is an immunoassay performed without either the binding substance or the detector substance being bound covalently or non-covalently to an insoluble support. It must be realized that the colloidal metal particles, to which ligands or antiligands are non-covalently bound thereby forming the detector substance, are considered as non-supportive since the detector substance freely passes through the pores of the porous support in the absence of analyte.

The analytes of the biological specimens tested in the present invention are carried in an appropriate liquid, normally the liquid present in the biological specimen. If the analyte to be assayed is contained in a biological specimen containing particulates that would not pass through the pores of the porous support, the biological specimen can be extracted to recover the appropriate analyte or filtered to remove non-analyte debris prior to complexing with the binding and detector substances. Therefore, if the biological specimen is normally solid in nature, such as in the form of cell or tissues, the specimen can be solubilized with any number of solubilizing procedures known to those skilled in the art, including but not limited to enzymatic digestion or solubilization with detergents followed by removal of particulate non-analyte components by filtration or centrifugation techniques.

The assay may be used to quickly determine the presence of a large variety of different analytes such as immunogens, for example proteins, glycoproteins, nucleoproteins and hormones (e.g. growth hormones and insulin). Other measurable analytes include haptens such as vitamins, drugs, glycosides, polypeptides and the like. Still other analytes include compounds that specifically interact with other compounds such as biotin and avidin, lectins and sugars, DNA fragments, RNA fragments and complementary DNA fragments and RNA fragments. A preferred analyte for assay in the present invention is C-reactive protein (CRP).

The binding substance of the present invention can be a ligand, an antiligand or a receptor capable of binding with the analyte desired to be measured. The term "ligand" describes any compound for which a receptor naturally exists or can be prepared. The terms "antiligand" and "receptor" can be used interchangeably and indicate any compounds or compositions that are capable of recognizing a particular spatial or polar organization of a molecule such as an epitopic site. Illustrative ligands are antibodies, enzymes, lectins, DNA fragments, RNA fragments and complementary DNA fragments and RNA fragments. Illustrative antiligands or receptors are antibodies, enzymes, lectins, DNA fragments, RNA fragments and complementary DNA fragments and RNA fragments.

The detector substance is either ligand or antiligand labeled with a colloidal metal such as colloidal gold, colloidal silver or colloidal copper and the like. The detector substance is preferably a colloidal gold or a colloidal silver labeled ligand, or a colloidal gold or a colloidal silver labeled antiligand, and most preferably colloidal gold labeled ligand or a colloidal gold labeled antiligand. Colloidal metal particles such as colloidal gold and silver particles can be prepared using many different procedures commercially available or otherwise known to those skilled in the art. In one prior art process colloidal gold particles having a particle size varying in a range from 5 nm to 100 nm are prepared during the reduction of chloroauric acid. While the present invention may employ any colloidal particle size capable of passing through the pore of the porous support, the preferred colloidal particle sizes for use in the present invention have a mean particle diameter of from about 10 to 40 nm, most preferably 20 to 25 nm. The colloidal particles may have an intermediate binder absorbed onto their surfaces prior the attachment of a ligand or an antiligand reagent, however, direct attachment is acceptable. The methods employed to produce the colloidal particulates and to produce labeled particulates by attaching the ligand and antiligands to the particulates are well known to those skilled in the art. Once the colloidal particulates have been labeled they are preferably centrifuged or filtered to control their particle size and to provide the detector substance.

The porous support used in the method of the present invention can be made of any water insoluble, porous material composed singly or in combination of cellulose acetate, nylon and other pore size controllable substrates, membranes and filters. The porous support must not contain materials that normally bind the analytes, such as proteins, the binding substance or the detector substance. The selection of the porous substrate is limited to porous supports capable of having the required controlled pore size ranging between about 0.2 to 12 microns, preferably ranging between about 0.8 to 1.2 microns for conducting the process of the present invention. The porous support should have a low, and preferably no nonspecific binding affinity for the analyte, the detector substance and the binding substance before and/or after treatment with reagents to reduce such affinity such as blocking agents, for example, dry milk, proteins, detergents or salts. Many commercially available porous membranes or films having such porosity, low nonspecific binding and controlled hydrophobicity, such as VERSAPOR and SUPOR available from Gelman Industries of Ann Arbor, Mich., are suitable for use in the present invention. The porous support can have any shape and thickness but is preferably flat and thin. The absorption, diffusion or filtration of the fluid phase of the test sample can be facilitated by the use of a fibrous or hydrophilic material as a layer in contact with the underside of the porous support. The flow of the fluid phase can also be controlled through the application of positive or negative pressure to the porous support.

While the test sample may be applied onto the entire surface of the porous support, the test sample is preferably deposited onto the surface of the porous support in a defined zone not greater then 25 $mm^2$, preferably between 0.5 and 25 $mm^2$, most preferably between 1.0 and 10 $mm^2$. The size of this defined zone exposed to contact with the test sample can be controlled by covering or sealing the porous support with a solid, water impervious, hydrophobic layer such as plastic, resinous laminate such that only one defined zone is available for contact with each application of test sample. Each porous support can have one or more noncontiguous defined zones for testing a plurality of test samples.

The preferred embodiment for performing the immunoassay of the present invention may vary according to the analyte in question. For example, where the analyte is a multivalent antigen and the test specimen is a fluid, the assay is performed in a non-competitive manner by simultaneously incubating the colloidal gold labeled antiligand detector substance, ligand binding substance, and the biological specimen together for an appropriate time period, such as one second to one hour, to form the test sample. The test sample containing an unknown amount of analyte is then poured or delivered by pipette onto the surface of the porous support. The bound and unbound gold labeled antiligand separate through and across the surface of the porous support leaving a complex, formed between the gold labeled antiligand bound to the analyte and the ligand binding substance, on the surface of the porous substrate for visual inspection. The presence of color on the surface of the porous substrate after application of the test sample onto the porous support is indicative of the presence of multivalent antigen in the test specimen.

The assay can also be performed as a competitive inhibition assay, particularly when the analyte is a hapten in a biological fluid. In this case the assay is performed by simultaneously incubating the test fluid with colloidal metal, preferably gold, labeled antiligand detector substance and hapten conjugate binding substance, or incubating the biological specimen with colloidal gold labeled hapten conjugate detector substance and an antiligand binding substance. After an appropriate incubation period the bound colloidal gold labeled detector substance that has complexed with the analyte, such as hapten and unbound or uncomplexed colloidal gold labeled detector substance, is separated by applying or contacting, such as by pouring or delivering by pipette, the test sample onto the surface of the porous support. The absence of color on the surface after application of the test sample onto the porous support is indicative of the presence of the hapten in the specimen. Competitive assays can also be performed for antigens or antibodies and are well known to those skilled in the art. For example, in the case of a serological test wherein the biological specimen is plasma, serum, or whole blood and the analyte is antibody, the specific target antigen is mixed with a specific antibody labeled with a colloidal metal such as gold. After appropriate incubation with the test serum, the reaction mixture is separated on the surface of the porous film. The absence of color is indicative of the presence of antibody in the specimen which has competitively inhibited the binding of the labeled gold antibody to the antigen.

An additional feature of the present invention resides in the use of the assay of the present invention as a kit. Such a kit is used for the qualitative or quantitative determination of an analyte in a biological sample and contains:
  (a) an insoluble porous support, said porous support being covered by a layer of water-impermeable material having at least one hole therein, and
  (b) a solution comprising: (i) a binding substance selected from the group consisting of a ligand and an antiligand capable of binding an analyte, and (ii) a detector substance selected from the group consisting of a colloidal metal labeled ligand and a colloidal metal labeled antiligand, wherein the ligand or the antiligand in the detector substance is capable of binding said analyte.

Preferably the colloidal metal is colloidal gold or colloidal silver and the kit additionally contains a sheet of hydrophilic material located adjacently beneath the porous support serving to enhance transverse diffusion of liquid in the test sample through the porous support.

Quantitative or semi-quantitative analysis is achieved by measuring the percent of reflectivity with a dedicated instrument such as a reflectometer or by visual inspection using a reference color chart displaying a range of color shades, each shade being indicative of an approximate respective concentration of analyte. The intensity of color displayed by the complex on the surface of the porous substrate is proportional to the concentration of the analyte in the test sample.

The test sample may also be diluted with an appropriate liquid prior to administration onto the porous substrate, however, the subsequent quantitative or semi-quantitative analysis must be adjusted by the appropriate dilution factor as is apparent to one skilled in the art.

One embodiment of a procedure and kit useful in conducting the non-captive substrate liquid phase immunoassay is shown in FIGS. 1 to 5.

Referring to FIG. 1, a container 1 has disposed therein a binding substance 3, a detector substance 5 containing a ligand or antiligand portion 7, and a colloidal metal particle portion 9, all in a liquid biological specimen 11 containing an analyte 13 capable of being bound by the binding substance 3 and the detector substance 5.

FIG. 2 shows the application of the contents of the container 1 in FIG. 1 through an opening 15 in a water impervious outer layer 17 onto the surface of a porous support layer 19 having pores 21 and optionally supported by a sheet 23 of hydrophilic material. FIG. 3 illustrates a complex 25 formed between the analyte 13, the binding substance 3 and the detector substance 5 on the surface of the porous membrane 19 for subsequent visual observation.

FIG. 4 illustrates the use of the method of the present invention in the absence of an analyte in the biological specimen. In this case, if analyte is absent in the biological specimen, no complex is formed thereby allowing the liquid biological specimen(not shown), the binding substance 3 and the detector substance 5 to pass completely through the pores 21 of the porous membrane substrate 19 into the hydrophilic sheet 23 where these substances are obscured from visual detection.

FIG. 5 is a top view of a test unit 27 having two openings 15 in the water impervious layer 17, thereby exposing a porous support layer 19. The optional hydrophilic sheet underneath the porous support layer 19 is not shown.

The present invention is further illustrated by the following examples which are not to be construed as limiting the invention to the specific procedures described therein.

EXAMPLE I

This example illustrates the utility of the test method for analyte present in both whole blood and plasma samples. A mixture of 17.2 micrograms of colloidal gold-labeled rabbit antibody to C-reactive protein (CRP) and 1.7 micrograms of unlabeled antibody to CRP was made in a buffer containing 0.2% sodium dodecyl sulfate, 0.25% Triton X-100, 0.01 M phosphate buffered saline having a pH of 7.4, and 0.5 milligrams per milliliter of bovine serum albumin. Fifty microliters of this antibody mixture was reacted with 10 microliters of whole blood or plasma containing various amounts of CRP (0, 16, 32, 64, 129 and 258 mg/L of CRP). The six reaction mixtures were incubated for three minutes at room temperature. Twenty-five microliters of each of the reaction mixtures were then transferred to cellulose acetate membrane of 0.8 micron pore size, allowed to soak through the membrane, and washed with one drop of phosphate buffered saline at pH of 7.4. The color intensity of the reaction was quantitated by reflectance spectrometry of the complex formed to the top of the porous support, and the results are displayed in Table 1. The color intensity of the whole blood and plasma samples is specified in units of reflectivity as measured by a Nycocard Reader reflectance meter manufactured by Nycomed Pharma A. S.

TABLE 1

| | COLOR INTENSITY (reflectivity units) | |
|---|---|---|
| mg/CRP | WHOLE BLOOD | PLASMA |
| 0 | 0.00 | 0.01 |
| 16 | 0.09 | 0.05 |
| 32 | 0.21 | 0.09 |
| 64 | 0.81 | 0.68 |
| 129 | 1.64 | 1.88 |
| 258 | 2.23 | 1.96 |

EXAMPLE II

This example illustrates determination of the optimum ratio of labeled to unlabeled antibody in the test method of the present invention. Mixtures of colloidal gold-labeled rabbit antibody against CRP and unlabeled rabbit antibody to CRP were prepared at four different ratios: 1:1.0, 1:1.2, 1:1.4, 1:1.5 (volume:volume). Fifty microliters of each mixture was then reacted with 10 microliters of five different specimens of whole blood, containing various amounts of CRP (0, 16, 32, 64, and 129 mg/L of CRP) as in Example 1, for three minutes. Twenty-five microliters of each of the reaction mixture was then transferred to cellulose acetate membrane of 0.8 micron pore size, allowed to soak through the membrane, and washed with one drop of phosphate buffered saline at pH of 7.4. The color intensity of each of the reactions was quantitated by reflectance spectrometry of the complex formed to the top of the porous support, and the results are displayed in Table 2.

TABLE 2

| | COLOR INTENSITY (reflectivity units) | | | |
|---|---|---|---|---|
| mg/L CRP | 1:1.0 (vol.:vol.) | 1:1.2 | 1:1.4 | 1:1.5 |
| 0 | 0.03 | 0.00 | 0.00 | 0.01 |
| 16 | 0.16 | 0.09 | 0.05 | 0.09 |
| 32 | 0.70 | 0.41 | 0.18 | 0.70 |
| 64 | 1.59 | 1.02 | 0.83 | 1.43 |
| 129 | 2.10 | 1.91 | 1.34 | 0.38 |

EXAMPLE III

This example illustrates the speed of reaction between the antibody and test analyte. A mixture of colloidal gold-labeled antibody and unlabeled antibody was made as described in Example I. Fifty microliters of this antibody mixture was added to six samples of 10 microliters of human plasma test analyte containing various amounts of CRP, (0, 16, 32, 64, 129, and 258 mg/L of CRP), and the reaction mixtures were incubated for varying periods of 30 seconds, 1 minute or 3 minutes at room temperature. Twenty-five microliters of each reaction mixture was applied to cellulose acetate membrane of 0.8 micron pore size, allowed to soak through the membrane, and washed with one drop of phosphate buffered saline, pH of 7.4. The color intensity of the reactions were quantitated as in the prior examples by reflectance spectrometry of the complex formed on the top of the porous support, and the results are displayed in Table 3.

TABLE 3

| | COLOR INTENSITY (reflectivity units) | | |
|---|---|---|---|
| mg/L CRP | 30 SEC | 1 MIN | 3 MIN |
| 0 | 0.00 | 0.01 | 0.00 |
| 16 | 0.00 | 0.05 | 0.02 |
| 32 | 0.02 | 0.08 | 0.09 |
| 64 | 0.09 | 0.21 | 0.68 |
| 129 | 0.32 | 1.45 | 1.88 |
| 258 | 0.45 | 2.13 | 1.96 |

EXAMPLE IV

This example illustrates the effect of membrane pore size on the final intensity of the reaction between antibody and test analyte. A mixture of colloidal gold-labeled antibody and unlabeled antibody was made and incubated with six specimens of human plasma test analyte containing various amounts of CRP (0, 16, 32, 64, 129, and 258 mg/L of CRP) for 3 minutes as described in Example I. Twenty-five microliters of each reaction mixture was applied to cellulose acetate membranes of 0.45, 0.8, 1.2 or 3.0 microns pore size, allowed to soak through intensity of the reactions were quantitated by as in the prior examples by reflectance spectrometry of the complex formed to the top of the porous support, and the results are displayed in Table 4.

TABLE 4

| | COLOR INTENSITY (reflectivity units) | | | |
|---|---|---|---|---|
| mg/L CRP | $0.45\mu$ | $0.8\mu$ | $1.2\mu$ | $3.0\mu$ |
| 0 | 0.00 | 0.00 | 0.02 | 0.01 |
| 16 | 0.05 | 0.07 | 0.05 | 0.07 |
| 32 | 0.08 | 0.09 | 0.07 | 0.08 |
| 64 | 0.56 | 0.68 | 0.33 | 0.27 |
| 129 | 1.43 | 1.88 | 0.95 | 0.80 |
| 258 | 1.64 | 1.96 | 0.75 | 0.54 |

EXAMPLE V

This example illustrates a semi-quantitative method of visual detection of the color development of a complexed analyte using a color chart calibrated with known levels of CRP. A mixture of colloidal gold-labeled antibody and unlabeled antibody was made and incubated with six specimens of whole blood containing various amounts of CRP as described in Example I. Twenty-five microliters of each reaction mix was applied to a porous cellulose acetate membrane, allowed to soak through the membrane, and washed with phosphate buffered saline. The color intensity of each of the reference reactions of the analyte complex formed on the surface of the porous support was compared to a color chart containing six separate colored regions calibrated to <10, 10, 25, 50, 100, and 200 mg/L of CRP, respectively. The results of this test, as displayed in Table V, illustrate that an approximation of analyte concentration can be quickly assessed by the method of the present invention.

TABLE 5

| Reference Analyte Complex mg/L CRP | Color Chart mg/L CRP |
| --- | --- |
| 0 | <10 |
| 8 | <10 |
| 12 | 10 |
| 16 | 10–25 |
| 28 | 25 |
| 81 | 100 |

We claim:

1. A method for the quantitative or qualitative detection of an analyte in a liquid biological specimen comprising the steps of:
   (a) forming a test sample by adding to a biological specimen, (i) a binding substrate in a liquid phase selected from the group consisting of a ligand and an antiligand which specifically binds the analyte, and (ii) a detector substance in a liquid phase selected from the group consisting of a colloidal metal labeled ligand and a colloidal metal labeled antiligand, to form a test sample containing a precipitable complex if the analyte is present and forming no such complex in the absence of the analyte in the biological specimen;
   (b) applying the test sample to a defined zone on a porous support, the support having a maximum effective pore size smaller than a complex formed between the analyte, the binding substance and the detector substance and having minimal effective pore size larger than each of the analyte, the binding substance and the detector substance if a precipitable complex with an analyte is not formed, so that the analyte, the binding substance and the detector all can pass through the support, no solid phase particles or insoluble components being introduced into the defined zone on the porous support; and
   (c) assessing the defined zone for color development caused by the formation of the complex formed by the analyte, the binding substance and the detector substance, the color development correlating with the presence of the analyte in the test sample.

2. The method of claim 1 performed in a non-competitive mode wherein a positive result is indicated by the presence of color development on the porous substrate.

3. The method of claim 1 performed in a competitive mode wherein a positive result is indicated by the absence of color development on the porous substrate.

4. The method of claim 1 wherein the biological specimen is solubilized prior to performing step (a).

5. The method of claim 1 wherein the defined zone on the porous support has an area between 0.5 and 25 mm$^2$.

6. The method of claim 1 wherein the detector substance is a colloidal gold labeled ligand.

7. The method of claim 1 wherein the detector substance is a colloidal gold labeled antiligand.

8. The method of claim 1 wherein the detector substance is a colloidal silver labeled ligand.

9. The method of claim 1 wherein the detector substance is a colloidal silver labeled antiligand.

10. The method of claim 1 wherein the colloidal metal in the detector substance has a mean particle diameter from about 10 to 40 nm.

11. The method of claim 1 wherein the test sample is applied to the defined zone on the porous support by flowing the test sample under the influence of positive or negative pressure.

12. The method of claim 1 wherein the binding substance is selected from the group consisting of antibodies, lectins, receptors, DNA fragments, and RNA fragments.

13. The method of claim 1 wherein the antiligand in the detector substance is a DNA or RNA fragment and the binding substance is complimentary DNA or RNA.

14. The method of claim 1 wherein the test sample is incubated after step (a) but prior to step (b).

15. The method of claim 1 wherein the biological specimen is diluted prior to step (a).

16. A method for the quantitative or qualitative detection of a C-reactive protein in a biological specimen of whole blood, serum, or plasma, comprising the steps of:
   (a) adding to a biological specimen a reagent solution consisting essentially of (i) a binding substance in the liquid phase comprising an unlabeled antibody to C-reactive protein, and (ii) a detector substance comprising an antibody to C-reactive protein said antibody labeled with colloidal gold, the reagent solution forming a precipitable complex with the C-reactive protein if the C-reactive protein is present and forming no such complex in the absence of the C-reactive protein in the biological specimen, the reagent solution free of solid phase particles;
   (b) applying the biological specimen and the added reagent solution to a defined zone on a porous support, the support having a maximum effective pore size smaller than a complex formed between the C-reactive protein, the binding substance and the detector substance and having minimal effective pore size larger than each of the substances contained within the reagent solution if a precipitable complex is not formed with the C-reactive protein; and
   (c) assessing the defined zone for color development and intensity caused by the formation of the complex formed by the C-reactive protein, the binding substance and the detector substance, the color development correlating with the presence of the C-reactive protein in the biological specimen.

17. A kit for the quantitative, semi-quantitative and qualitative determination of an analyte in a biological sample consisting essentially of:
   (a) an insoluble porous support, said porous support being covered by a layer of water-impermeable material having at least one hole therein, the porous support having an maximum effective pore size smaller than a complex formed between the analyte, the binding substance and the detector substance and having minimal effective pore size larger than each of the analyte, the binding substance and the detector substance if a precipitable complex with an analyte is not formed, so that the analyte, the binding substance and the detector all can pass through the support;
   (b) a solution comprising: (i) a binding substance in liquid phase selected from the group consisting of a ligand and an antiligand which specifically binds to an analyte, and (ii) a detector substance selected from the group consisting of a colloidal gold labeled ligand, a colloidal silver labeled ligand, and colloidal gold labeled antiligand and a colloidal silver labeled antiligand, wherein the antiligand or the ligand in the detector substance binds to the analyte, all components of the solution being small enough to pass through the effective pore size of the pores in the porous support if binding of the binding substance to the analyte does not occur the solution free of solid phase particles.

18. The kit according to claim 17 wherein the porous support has located adjacently beneath a sheet of hydrophilic material serving to enhance transverse diffusion of liquid through the porous support.

19. The kit according to claim 17 wherein the hole has an area between 0.5 and 25 mm$^2$.

20. The kit according to claim 17 wherein the binding substance is selected from the group consisting of antibodies, lectins, receptors, DNA fragments, and RNA fragments.

21. The kit according to claim 17 wherein the analyte is C-reactive protein.

* * * * *

UNITED STATES PATENT AND TRADEMARK OFFICE
CERTIFICATE OF CORRECTION

PATENT NO.     : 6,632,603 B1
DATED          : October 14, 2003
INVENTOR(S)    : Thomas T. Hubscher and Erik P. Lillehoj It is certified that error appears in the above-identified patent and that said Letters Patent is hereby corrected as shown below:

<u>Title page,</u>
Insert: -- [73] Assignee: Dexall Biomedical Labs, Inc. --

Signed and Sealed this

Sixth Day of January, 2004

JAMES E. ROGAN
*Director of the United States Patent and Trademark Office*